(12) United States Patent
Betts

(10) Patent No.: US 9,017,304 B1
(45) Date of Patent: Apr. 28, 2015

(54) FEMININE SANITARY NAPKIN

(76) Inventor: Joyce Betts, Huntsville, AL (US)

(*) Notice: Subject to any disclaimer, the term of this patent is extended or adjusted under 35 U.S.C. 154(b) by 766 days.

(21) Appl. No.: 12/931,134

(22) Filed: Jan. 26, 2011

(51) Int. Cl.
A61F 13/15 (2006.01)
A61F 13/472 (2006.01)
A61F 13/474 (2006.01)

(52) U.S. Cl.
CPC ......... *A61F 13/47227* (2013.01); *A61F 13/474* (2013.01); *A61F 2013/4729* (2013.01)

(58) Field of Classification Search
CPC . A61F 13/472; A61F 13/47; A61F 13/47209; A61F 13/47218; A61F 13/47227; A61F 13/474; A61F 2013/4729
USPC ........ 604/385.101, 361, 385.01, 363, 385.17, 604/385.03, 385.04
See application file for complete search history.

(56) References Cited

U.S. PATENT DOCUMENTS

| | | | | |
|---|---|---|---|---|
| 4,046,147 A * | 9/1977 | Berg | ...................... | 604/385.201 |
| 5,290,262 A * | 3/1994 | Vukos et al. | ............. | 604/385.17 |
| 5,383,868 A * | 1/1995 | Hyun | ....................... | 604/385.17 |
| 5,743,896 A * | 4/1998 | Parker | ...................... | 604/385.01 |
| 6,059,763 A * | 5/2000 | Brown | ..................... | 604/385.17 |
| 6,425,890 B1 * | 7/2002 | Samuelsson et al. | .... | 604/385.17 |
| 7,122,023 B1 * | 10/2006 | Hinoki | ................... | 604/385.101 |
| 7,368,627 B1 * | 5/2008 | Widlund | ...................... | 604/378 |
| 8,167,860 B1 * | 5/2012 | Siegel | ...................... | 604/385.04 |
| D686,727 S * | 7/2013 | Betts | .......................... | D24/125 |
| 2002/0065497 A1 * | 5/2002 | Kolby-Falk | ................... | 604/368 |
| 2008/0172019 A1 * | 7/2008 | Chien | ..................... | 604/385.04 |

* cited by examiner

Primary Examiner — Lynne Anderson
Assistant Examiner — Bradley Philips
(74) Attorney, Agent, or Firm — Rodgers & Rodgers

(57) ABSTRACT

A sanitary napkin includes a multi-layered primary pad having an intermediate absorbent layer with a cavity formed therein and a liquid permeable top layer overlying the absorbent layer with a slit formed therein. A cavity is formed in the absorbent layer and is positioned below the slit. An auxiliary pad has an upstanding plug with the auxiliary pad disposed partially in the cavity and the plug extending through the slit.

3 Claims, 1 Drawing Sheet

FEMININE SANITARY NAPKIN

BACKGROUND OF THE INVENTION

Various types of sanitary napkins have been used for many years to retain a woman's bodily secretions such as menses and blood. It is especially problematic when a user is lying down because bodily secretions tend to flow from the body in all directions causing stains on garments and bed linens. One widely used napkin is a tampon to absorb bodily fluids internally. Another is an absorbent pad worn externally. Both types of napkins absorb bodily fluid to a degree but often do not completely absorb the fluids thereby causing undesirable leakage. It is known to combine features of both external and internal sanitary napkins, but this results in a napkin which is often uncomfortable and is not well suited to conform to a wide range of physical characteristics.

BRIEF SUMMARY OF THE INVENTION

By this invention, a sanitary napkin is provided and includes a multi-layered primary pad having a permeable top layer, an intermediate absorbent layer and a liquid impermeable bottom layer. A slit is formed in the primary top layer with a cavity formed in the absorbent layer and disposed below the slit. A multi-layer auxiliary pad is provided having a top layer, intermediate absorbent layer and a lower liquid impermeable layer with a portion of the absorbent layer extending upwardly in the form of a plug. The auxiliary pad is disposed in the cavity with the plug extending through the slit formed in the primary pad top layer. In addition, the end edges of the auxiliary pad are spaced from the end edges of the cavity to provide sliding adjustability for the plug.

DETAILED DESCRIPTION OF THE INVENTION

Figure 1:
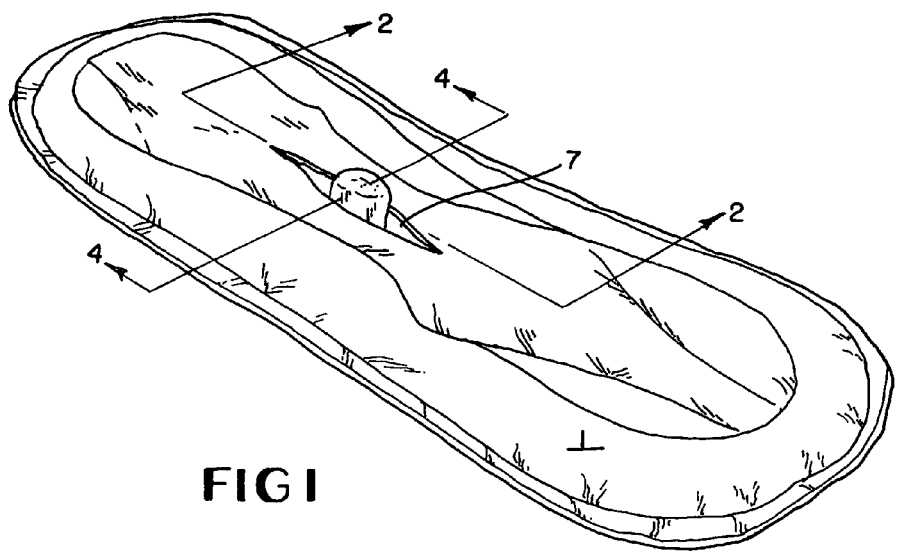
FIG. 1 is a perspective view of a sanitary napkin in accordance with this invention.
Figure 2:
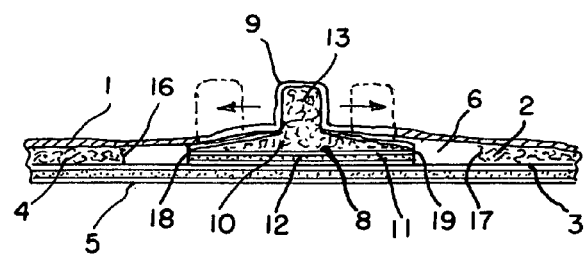
FIG. 2 is an elevational view taken along the line 2-2 in FIG. 1.
Figure 3:
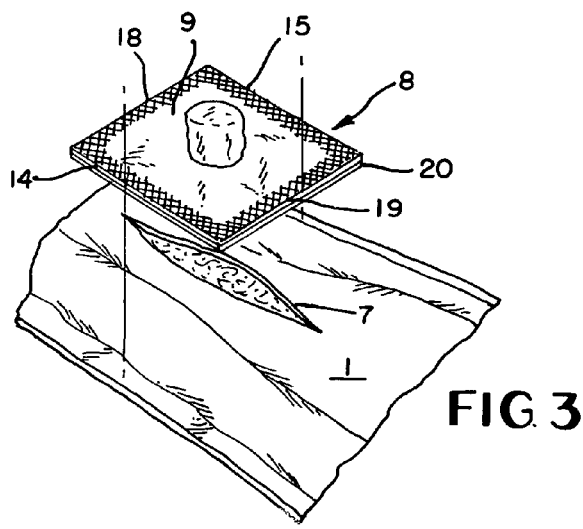
FIG. 3 is a partially exploded perspective view of the sanitary napkin.
Figure 4:
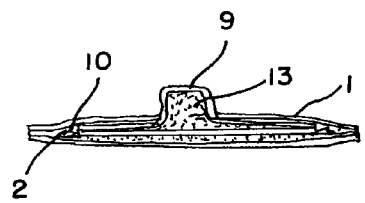
FIG. 4 is an elevational view taken along the lines 4-4 in FIG. 1.

In the drawings and with particular reference to FIGS. 1 and 2, the feminine sanitary napkin, according to this invention, is shown and includes a primary pad having liquid permeable top layer 1 with absorbent relatively thick intermediate layer 2 disposed therebelow. Liquid impermeable bottom layer 3 is disposed below absorbent layer 2 and adhesive layer 4 is disposed below liquid impermeable layer 3. All four layers are essentially disposed in flat face contacting relation and sealed around the peripheral edges by means of heat sealing and the like. Adhesive layer 4 is provided to adhere to a user's clothes, as is well known. Removable cover sheet 5 overlies adhesive layer 4, also as is well known. Absorbent layer 2 includes cavity 6 formed therein with slit 7 formed in top layer 1 and disposed immediately above cavity 6.

According to this invention, an auxiliary pad is provided, generally designated by the numeral 8, and includes liquid permeable top layer 9, auxiliary absorbent layer 10, liquid impermeable layer 11 and adhesive layer 12. As viewed in FIG. 2, absorbent layer 10 includes an upstanding plug 13 with top layer 9 extending completely over plug 13. In the drawings, auxiliary pad 8 is shown as being square in configuration but can embody other shapes, as desired.

Most importantly, auxiliary pad 8 must conform to the configuration of cavity 6 so that it will slide in the longitudinal direction but not the lateral direction of the napkin. Side edges 14 and 15 of auxiliary pad 8 are in close proximity to the side edges of cavity 6 which prevents lateral displacement of auxiliary pad 8. So that auxiliary pad 8 can slide in cavity 6, the end edges 16 and 17 of cavity 6 are spaced, respectively, from end edges 18 and 19 of auxiliary pad 8. By this means, auxiliary pad 8 is slidable longitudinally in the primary pad within cavity 6 which allows the napkin to be maneuvered so as to be placed in the most comfortable position for the user while maintaining auxiliary pad 8 in its optimum position for purpose of absorbing menses and blood.

Auxiliary pad 8 can be used by itself which requires that paper cover 20 be removed from adhesive layer 12 and plug 13 inserted internally. Of course, to be fully effective, the entire sanitary napkin must be utilized wherein auxiliary pad 8 is inserted into cavity 6 so that plug 13 extends upwardly through slit 7. Plug 13 is then placed internally in the user whereby the entire sanitary napkin acts to fully absorb any bodily secretions.

Therefore, by this invention, a sanitary napkin is provided which effectively absorbs all the bodily secretions of the user and, at the same time, is adjustable to conform to the particular physical characteristics of the user.

The invention claimed is:

1. A sanitary napkin for absorption of a user's bodily fluids comprising a primary pad, said primary pad including a top liquid permeable layer and an absorbent layer disposed therebelow, a slit formed in said top layer, an auxiliary pad having an auxiliary absorbent layer disposed below said top liquid permeable layer, a plug extending upwardly from said auxiliary absorbent layer through said slit, a cavity formed entirely in said absorbent layer, said auxiliary pad disposed completely within said cavity, said plug sized to extend substantially internally of the user, said cavity comprising spaced side edges and spaced end edges such that only the absorbent layer forms each of the cavity's side and end edges, said auxiliary pad comprising spaced side edges and spaced end edges, and said end edges of said auxiliary pad being spaced respectively from said end edges of said cavity.

2. A sanitary napkin according to claim 1 wherein said side edges of said auxiliary pad are in substantial abutting relation respectively with said side edges of said cavity.

3. A sanitary napkin according to claim 1 wherein an auxiliary liquid permeable top layer overlies said plug.

\* \* \* \* \*